(12) United States Patent
Katerkamp et al.

(10) Patent No.: US 6,441,055 B1
(45) Date of Patent: Aug. 27, 2002

(54) SENSOR MEMBRANE FOR DETERMINING OXYGEN CONCENTRATIONS AND PROCESS FOR THE PREPARATION THEREOF

(75) Inventors: Andreas Katerkamp, Münster; Maria Hiegemann, Sendenhorst; Erk Gedig, Münster, all of (DE)

(73) Assignee: Institut fur Chemo-und Biosensorik Munster e.V. (DE)

( * ) Notice: Subject to any disclaimer, the term of this patent is extended or adjusted under 35 U.S.C. 154(b) by 0 days.

(21) Appl. No.: 09/744,091

(22) PCT Filed: Jul. 12, 1999

(86) PCT No.: PCT/DE99/02168

§ 371 (c)(1),
(2), (4) Date: Feb. 23, 2001

(87) PCT Pub. No.: WO00/04367

PCT Pub. Date: Jan. 27, 2000

(30) Foreign Application Priority Data

Jul. 15, 1998 (DE) .......................................... 198 31 770

(51) Int. Cl.⁷ .................................................. C08J 9/26
(52) U.S. Cl. ............................. 521/61; 521/64; 521/89; 521/92; 521/93
(58) Field of Search ............................. 521/61, 64, 89, 521/92, 93

(56) References Cited

U.S. PATENT DOCUMENTS

| | | |
|---|---|---|
| 4,705,545 A | 11/1987 | Polak et al. |
| 5,030,420 A | 7/1991 | Bacon et al. |
| 5,414,117 A | 5/1995 | Armand et al. |
| 5,580,527 A | 12/1996 | Bell et al. |

FOREIGN PATENT DOCUMENTS

| | | |
|---|---|---|
| DE | 9200389.3 | 5/1992 |
| EP | 109958 | 5/1984 |
| EP | 300900 | 1/1989 |
| EP | 300990 | 1/1989 |
| EP | 0 585 212 | 3/1994 |

OTHER PUBLICATIONS

Hassan et al., "Miniaturized Verapamil Solid–State Potentiometric Sensors Based on Native Ionic Polymers," Chemical Abstracts Service, Columbus, Ohio (XP002127582 (1999)).

Wolfbeis, Otto S. (Editor) *Fiber Optic Chemical Sensors and Biosensors*, vol. II, CRC Press, Boca Raton, FL (1991) pp. 28–29.

*Primary Examiner*—John M. Cooney, Jr.
(74) *Attorney, Agent, or Firm*—Leydig, Voit & Mayer, Ltd.

(57) ABSTRACT

The invention relates to sensor membranes for determining oxygen concentrations and to a process for the preparation thereof, in which, in a polymer matrix which is permeable to oxygen, an indicator is present whose optical and physicochemical properties can be influenced by the respective analytes. Starting from the disadvantages of known sensor membranes, it is the object of the invention to provide a sensor membrane which is thermally and also dimensionally stable, and can be prepared simply and flexibly. This object is achieved according to the invention in that the polymer matrix which contains the optical oxygen indicator is formed from a polymer containing sulfur, preferably in the main chain, particularly preferably containing sulfide and/or sulfone functionalities in the main chain.

17 Claims, 2 Drawing Sheets

Uvinul 4049 H

Uvinul 4050 H

Uvinul 5050 H

SENSOR MEMBRANE FOR DETERMINING OXYGEN CONCENTRATIONS AND PROCESS FOR THE PREPARATION THEREOF

This application is the U.S. National Phase of international patent application PCT/DE99/02168, filed on Jul. 12, 1999, and claiming priority to German patent application Ser. No. 198 31 770.0, filed July 15, 1998, hereby incorporated by reference.

The invention relates to a sensor membrane and to a process for the preparation thereof.

BACKGROUND OF THE INVENTION

Thus, amongst others, EP 0 585 212 A2, for example, describes the sensor membrane of an optical sensor with which $O_2$, $H_2O_2$, $SO_2$ or halogenated hydrocarbons can be detected in a sample. Here, an indicator substance has been incorporated into an appropriate polymer matrix, which indicator substance changes its optical properties as a result of the presence of said analytes. Thus, for example, the known luminescence quenching, i.e. a change in the luminescence intensity which arises as a result of contact of the analytes suitable therefor with the corresponding indicator, can be exploited and, accordingly, the respective analyte concentration can be measured. However, a change in the luminescence fading time or the optical absorption of light waves are also suitable evaluatable parameters.

The prior art discloses various polymers which are more or less suitable for the preparation of a sensor membrane. These polymers are subject to a number of basic prerequisites. These are at least a certain degree of permeability for the respective analytes, a possibility of incorporating the indicator into the polymer matrix without the latter losing its function, and transparency for the wavelength ranges of the measurement light which are used.

The polymers described hitherto for the preparation of a sensor membrane for determining, for example, oxygen are, for example, cellulose, polystyrenes, polytetrahydrofuran and derivatives thereof (EP 0 585 212 A2), PVC (U.S. Pat. No. 4,003,707) and PVC containing plasticizer (U.S. Pat. No. 4,752,115), partially fluorinated polyurethanes (WO 95 08 107, WO 93 18 391, U.S. Pat. No. 5,453,248), silicones in various modifications (U.S. Pat. No. 4,003,707, U.S. Pat. No. 5,0303,420, WO 95 22 759, WO 94 04 241, WO 96 37 768) in which the indicator is reportedly present in dissolved form. By contrast, polymers to which the indicator has been coupled by a chemical bond (U.S. Pat. No. 5,580,527) or else the indicator has been absorbed to a particle of, for example, silicon dioxide, which has then been incorporated into a polymer matrix (U.S. Pat. No. 4,003,707) are also described. A sensor membrane based on a ceramic as matrix material has also been described (U.S. Pat. No. 5,490,490).

However, polymers described and used hitherto do not have further properties essential for many applications. This refers essentially to their relatively low mechanical and thermal stability, in which case it is to be noted that for many applications a single or repeated sterilization, e.g. with water vapor, may be required. However, the high temperatures which arise during this process lead in the case of the known materials to undesired changes in their physicochemical and optical properties, rendering them unsuitable for such applications.

A further disadvantage arises from the poor fixing of the sensitive indicator, e.g. the transition metal complexes, in the polymer matrices used. Said complexes are poorly soluble in hydrophobic, relatively soft gas permeable silicone membranes, for which reason they have to be adsorbed to filler materials. The heterogeneous distribution of additionally light-scattering particles has optical disadvantages. The transition metal complexes can be washed out of polyanionic materials relatively easily since they exhibit ion exchanger behavior and are hydrophilic. Moreover, the latter materials have the disadvantage that they can be penetrated by the mostly aqueous sample solution, resulting in poor chemoselectivity to the substances dissolved in the aqueous sample solution to which the indicator exhibits cross sensitivity. Furthermore, the analyte-indicated changes in the transition metal complexes in an ionic environment are often irreversible, for which reason use in a reversibly operating sensor is not possible.

BRIEF SUMMARY OF THE INVENTION

This object preferably is achieved according to the invention. Advantageous embodiments and developments of the invention will be apparent from the description of the invention provided herein.

Figure 1:
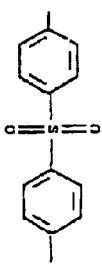
FIG. 1 is a classification of known sulfur polymers showing sulfur polymers on the basis of diphenyl sulfone and diphenyl sulfide (see, e.g., the book by Hans Domininghaus, *Plastics and their Properties*, Springer Verlag, Berlin, Hamburg, New York, (1998)). For example, some special sulfur polymers are mentioned with trade name and producer.

For the sensor membranes according to the invention, either exclusively sulfur polymers or a mixture thereof with other polymers, e.g. silicone or PVC or a mixture are used for the polymer matrix, preference being given to using polymers containing sulfur in the main chain.

DETAILED DESCRIPTION OF THE INVENTION

Advantageously, it is possible to use a polymer matrix which consists predominantly of polymers containing sulfur in the main chain, and the sulfur is incorporated into the main chain of the polymer in the form of sulfide or sulfone. It is also possible to use polymers based on diphenyl sulfide and/or diphenyl sulfone or else derivatives thereof. In contrast to solution routes described hitherto, in the sensor membranes according to the invention polymeric sulfide and/or sulfone functionalities are used for the first time in a targeted manner to immobilize the analyte-sensitive transition metal complexes. As a result of their high Lewis basicity, the uncharged sulfide and/or sulfone groups and also, to a certain extent, the aromatic $\pi$ electrons of the phenyl substituents interact with the cationic transition metal complexes. This leads to said complexes being homogeneously dispersed in the polymer membrane, where they are stabilized against being washed out. On the other hand, however, the attractive interaction is still so slight that the oxygen-induced transition of the complexes from the quenched to the unquenched state and vice versa is completely reversible. Moreover, due to their hydrophobicity, the polymers which can be used according to the invention significantly increase the chemoselectivity of the oxygen-sensitive membranes since they are selectively permeable only for hydrophobic substances—in practice i.e. in particular gases.

The desired combination of transition-metal-complex-solubilizing properties and a sufficiently hydrophobic character has, however, only hitherto been achieved by certain cellulose derivatives, polystyrene and polytetrahydrofuran (EP 0 585 212). Apart from the transition metal complexes having a susceptibility toward wash-out which is still too high, they also, however, have the disadvantages of poor thermal and mechanical stability. Appropriate experiments show that the polymers which can be used according to the invention for sensory applications are significantly more suitable under conditions simulating those in practice, that they are significantly harder and more dimensionally stable, and exhibit low water absorption but nevertheless good oxygen permeability. In continuous operation they are able to readily withstand temperatures up to 160° C., meaning that a superheated-steam sterilization can be survived easily without damage, and the optical and mechanical properties are retained.

A further advantage of the polymers which can be used according to the invention consists in the fact that they can be dissolved in very few organic solvents, these including those which are also able to dissolve suitable indicators.

The advantageous properties mentioned hitherto mean that such a sensor membrane is suitable for a wide variety of applications in the field of medicine and biotechnology.

The sensor membrane according to the invention also becomes neither brittle nor cracked following repeated cost-effective steam sterilization (auto-claving), it retains its flexibility, and its adhesion to any support which may be used is likewise not impaired.

Due to the high mechanical stability of the polymers to be used according to the invention, it is also no longer obligatory to use a suitable support for such a membrane. This gives rise to entirely new use or further processing possibilities. Thus, a sensor membrane without support is very thin and flexible and can, e.g. provided with an adhesion promoter, be fixed to various measurement sites. This is particularly advantageous in the case of measurement sites to which the membrane cannot be applied by coating techniques, such as dip coating, imprinting, dropping, spraying or the like.

The hitherto mentioned advantageous properties of the polymers to be used according to the invention also lead, however, to the fact that, at relatively high temperatures, the indicator included in the polymer matrix achieves no greater mobility, for example in the case of polymers whose melting point is lower than that of the polymers to be used according to the invention, and accordingly no agglomerates or clusters of the indicator are formed. Possible agglomeration or clustering of the indicator impairs Ru (II) tris(4,7-diphenyl-1,10-phenanthroline)dichloride is particularly suitable; this is likewise very readily soluble in mono- or polychlorinated solvents.

A sensor membrane for oxygen according to the invention can therefore be prepared directly by dissolving the indicator RU(II) tris(4,7-diphenyl-1,10-phenanthroline)dichloride and a polymer to be used according to the invention, such as polysulfone, in dichloromethane. Subsequently, this solution of solvent, indicator and polymer is then applied to a support by dropping, spraying, dip coating, dispensing, imprinting, spin coating or similar in the form of a thin liquid film. Removal of the solvent by evaporation, e.g. at room temperature, produces a thin polymer membrane with indicator dissolved therein. Removal of the solvent by evaporation can, however, also be carried out at higher temperatures up to the melting point of the polymers. It has also proven very favorable to carry out the evaporation of a solvent, for example dichloromethane, in a gas environment in which dichloromethane is already present in gaseous form. This results in slow evaporation, as a result of which a very homogeneous and transparent polymer membrane forms. Such a sensor membrane can then be used together with the support material for the measurement of oxygen concentrations. The support material which may be used is the end of an optical waveguide, although it is also possible to use a thinner transparent polymer film of, for example, polycarbonate, polyacrylate or PMMA or glass plates as support material.

In principle, however, the sensor membrane can also which is oxygen-permeable but nontransparent for ambient light prevents this, and at the same time the environment of the measurement site would be protected from the measurement light and/or luminescent light, which is very important in some medical or biotechnological applications.

Surprisingly, it has been found that in all sensor membranes produced on the basis of, the polymers to be used according to the invention by the process described, indicators based on the Ru(II) complexes are present in homogeneously dispersed form in the sensor membrane. No agglomerates or clusters of Ru(II) complexes have been found. Even after repeated steam sterilization of the sensor membrane no agglomerates or clusters have been found. Furthermore, it was also surprisingly found that the optical and sensory properties of the Ru(II) complexes do not change at all as a result of repeated steam sterilization. This is an unexpected result since in the case of the sensor membranes known hitherto a change in the optical and sensory properties following steam sterilization has been measured.

Comparative experiments have also shown that the sensor membranes according to the invention prepared in this way have significantly lower wash-out behavior of the immobilized indicator.

The long-term stability of the sensor membranes according to the invention can be increased significantly by additionally adding to the polymer matrix free-radical scavengers or else light protection stabilizers which prevent, or at least hinder, destruction of the polymer and of the indicator as a result of the effect of light, meaning that use of the sensor membranes can be achieved over a relatively long period compared with the solutions known hitherto. The addition of the free-radical scavengers or also light protection stabilizers counters the known phenomenon that, as a result of the effect of light, even if only small amounts of free radicals and hydroperoxides are produced, the polymer and the indicator are attacked and converted chemically. Suitable free-radical scavengers or else light protection stabilizers have proven to be those which are chosen from the group of sterically hindered amines (HALS=hindered amine light stabilizer) which, unlike customary light protection agents, are not based on the absorption of the irradiated light or on the quenching of the absorbed light, but essentially on the ability to scavenge or to replace free radicals and hydroperoxides formed during the photodegradation of polymers. This on the one hand prevents further degradation of the polymers and thus achieves stabilization of the microenvironment of the indicator and at the same time protects the indicator from chemical attack by free radicals and hydroperoxides. In addition, singlet oxygen is quenched by free-radical scavengers or also light protection stabilizers based on sterically hindered amines. As is known, singlet oxygen leads to a poisoning of a sensor membrane for the detection of oxygen based on Ru(III) complexes. Thus, such free-radical scavengers or else light protection stabilizers are particularly suitable for the long-term stabilization of oxygen sensor membranes.

Figure 2:
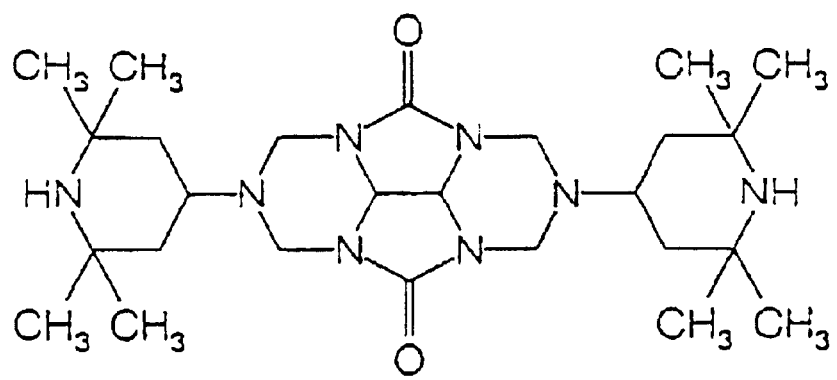
FIG. 2 illustrates several sterically hindered amines (HALS compounds) with the trade name Uvinul (e.g., Uvinul 4049 H, Uvinul 4050 H, Uvinul 5050 H), commercially available from Bayer. Such HALS compounds can be used, for example, for light protection stabilization.
Figure 2:
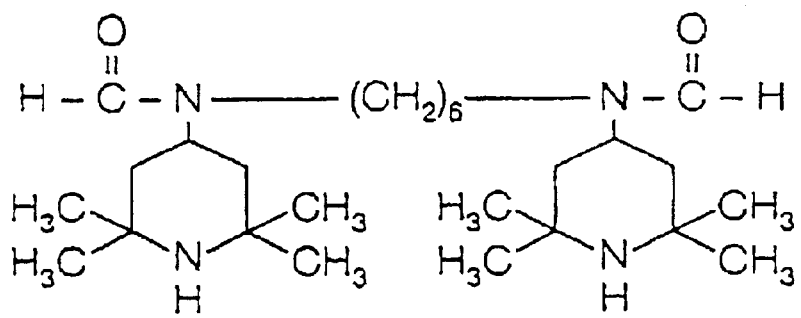
Figure 2:
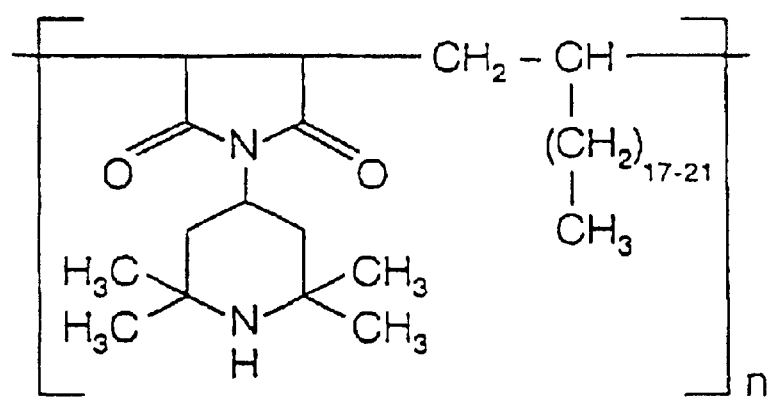

A detailed description of free-radical scavengers or also light protection stabilizers based on sterically hindered amines is given in "R. Gächter, H. Muller, Plastics Additives Handbook, Carl Hanser Verlag Munich, Vienna, 1989". A suitable HALS compound which has proven successful is the product Uvinul 4050 H from Bayer, which can be added to the dissolved polymer/transition metal complex mixture and be used in a proportion by weight of 0.1 to 0.5% of the polymer. FIG. 2 shows a number of HALS compounds, such as, for example, Uvinul 4050 H. The compound Uvinul 4050 H is very readily soluble in dichloromethane and can be mixed into the solution, already described, of dichloromethane, Ru(II) tris(4,7-diphenyl-1,10-phenanthroline)dichloride and polysulfone. The further processing of the sensor membrane can then be carried out, as described.

The invention will be illustrated in more detail below using an example of an oxygen-sensitive sensor membrane.

A stock solution No. 1 of 10 ml dichloromethane and 5.036 mg of Ru(II) tris(4,7-diphenyl-1,10-phenanthroline) dichloride is prepared. A stock solution No. 2 of 2 514 g of polysulfone having an average molar mass of 27 000 and 30 ml of dichloromethane is also prepared. The stock solution No. 2 is stirred for 24 hours at room temperature. 5 ml of the stock solution No. 1 and 15 ml of the stock solution No. 2 are mixed in to prepare the sensor membrane stock solution. To improve the long-term stability of the sensor membrane, 7 542 mg of the HALS compound Uvinul 4050 H is added to the sensor membrane.

Dropping 40 µl of the sensor membrane stock solution onto a glass plate and immediately covering the glass plate with a petri dish produces a sensor membrane. After 20 minutes, the petri dish is removed and the glass plate with membrane is heat-treated for 2 hours at 80° C. The membrane can then be removed from the glass plate and be applied to various measurement sites by adhesion.

The described sensor membrane solution is used to coat the front face of an optical waveguide made of glass. Immersion of the front face of the optical waveguide into this solution and slow evaporation of the solvent, where, for this, the front face should be held about 2 to 3 mm over the sensor membrane stock solution for about 1 minute, produces a readily adhering sensor membrane on the front face of the optical waveguide.

What is claimed is:

1. A sensor membrane for determining oxygen concentrations, in which, in a polymer matrix permeable to oxygen, an indicator is present whose optical and physico-chemical properties can be influenced by oxygen, wherein the polymer matrix consists predominantly of sulfur polymers in which the sulfur is incorporated into the main chain of the polymer in the form of sulfide or sulfone.

2. The sensor membrane as claimed in claim 1, wherein the polymer matrix consists predominantly of a polymer in which diphenyl sulfide and/or diphenyl sulfone or derivatives thereof are incorporated in the main chain of the polymer.

3. The sensor membrane as claimed in claim 1 or 2, wherein the polymer matrix additionally contains at least one chemical free-radical scavenger and/or light protection stabilizer.

4. The sensor membrane as claimed in claim 3, wherein the free-radical scavenger and/or light protection stabilizer has/have sterically hindered amines as functional groups.

5. The sensor membrane as claimed in any of claims 1 to 4, wherein the indicator is an oxygen-sensitive Ru, Os, Ir, Rh, Pd, Pt or Re transition metal complex.

6. The sensor membrane as claimed in any of claims 1 to 5, wherein the oxygen-sensitive indicator is Ru(II) tris(4,7-diphenyl-1,10-phenanthroline)dichloride.

7. The sensor membrane as claimed in any of claims 1 to 6, wherein the sensor membrane is applied to a support.

8. The sensor membrane as claimed in claim 7, wherein there is an adhesion promoter layer on the support.

9. The sensor membrane as claimed in claim 7, wherein the support is an adhesive film.

10. The sensor membrane as claimed in claim 7, wherein the sensor membrane can be used detached from the support, without the support.

11. The sensor membrane as claimed in claim 10, wherein the sensor membrane without support is coated with an adhesive film.

12. The sensor membrane as claimed in claim 1, wherein an oxygen-permeable layer is applied to one side of the sensor membrane.

13. The sensor membrane as claimed in claim 12, wherein the oxygen-permeable layer consists of a material which is optically non-transparent for the measurement and/or luminescent light.

14. A process for the preparation of a sensor membrane as claimed in claim 1, comprising forming the polymer matrix predominantly from sulfur polymers, wherein the sulfur is incorporated in the form of the sulfide or sulfone in the main chain, and the indicator in a solvent and applying this solution to a support and then removing the solvent.

15. The process as claimed in claim 14, wherein chemical free-radical scavengers and/or light protection stabilizers are additionally added to the solution prepared from polymer matrix, indicator and solvent.

16. The process as claimed in claim 14, wherein the solution comprising polymer matrix and indicator is applied to the support by dropping, spraying, dip coating, dispensing, spin coating or imprinting.

17. A method for determining the oxygen concentration in liquid and gaseous media, the method comprising utilizing the sensor membrane as claimed in claim 1.

* * * * *

UNITED STATES PATENT AND TRADEMARK OFFICE
CERTIFICATE OF CORRECTION

PATENT NO.     : 6,441,055 B1
DATED          : August 27, 2002
INVENTOR(S)    : Katerkamp et al.

It is certified that error appears in the above-identified patent and that said Letters Patent is hereby corrected as shown below:

Column 5,
Line 53, please delete ", in which, in" and substitute therefor -- comprising --.
Lines 54 and 55, delete "is present whose optical and physicochemical properties" and substitute therefor -- which is present in said polymer matrix, said indicator having optical and physicochemical properties that --.

Column 6,
Line 6, please change the dependency from "claim 1 or 2" to -- claim 1 --.
Lines 13-14, please change the dependency from "any of claims 1 to 4" to -- claim 1 --.
Lines 16-17, please change the dependency from "any of claims 1 to 5" to -- claim 1 --.
Lines 19-20, please change the dependency from "any of claims 1 to 6" to -- claim 1 --.

Signed and Sealed this

Seventh Day of January, 2003

JAMES E. ROGAN
*Director of the United States Patent and Trademark Office*